United States Patent [19]

Urano et al.

[11] Patent Number: 5,117,044

[45] Date of Patent: May 26, 1992

[54] POLYMERIZABLE COMPOUND AND POLYMER THEREFROM

[75] Inventors: Satoshi Urano, Tsuzuki; Kei Aoki, Ikoma; Nobuaki Tomita, Nara; Hirohiko Mori, Settsu, all of Japan

[73] Assignee: Nippon Paint Co., Ltd., Osaka, Japan

[21] Appl. No.: 464,121

[22] Filed: Jan. 12, 1990

[30] Foreign Application Priority Data

Jan. 12, 1989 [JP] Japan ................. 1-7031
Dec. 7, 1989 [JP] Japan ................. 1-318504

[51] Int. Cl.$^5$ .............................. C07C 69/34
[52] U.S. Cl. ............................ 560/193; 526/280; 526/285; 556/449; 560/190; 560/201
[58] Field of Search ............ 560/201, 190, 193; 526/285, 280; 556/253

[56] References Cited

U.S. PATENT DOCUMENTS

2,153,987  4/1939  Nicodemus et al. ............ 560/201
3,484,479 12/1969  Rinkler et al. ................. 562/923

FOREIGN PATENT DOCUMENTS

46-01716  1/1971  Japan .
59-5061  11/1947  United Kingdom .

*Primary Examiner*—Joseph L. Schofer
*Assistant Examiner*—Fred Zitomer
*Attorney, Agent, or Firm*—Wegner, Cantor, Mueller & Player

[57] ABSTRACT

The invention provides a polymerizable compound represented by the formula (I):

$$A-X-COCOOR_1$$

wherein A represents a $C_1$-$C_{18}$ alkenyl, alkynyl, alkenylaryl or alkenylaralkyl group, or a group represented by 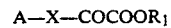
wherein $R_2$ and $R_3$, which are the same or different, represent a hydrogen atom or a $C_1$-$C_5$ alkyl group, Y represents an oxygen atom or $-NR_4-$, in which $R_4$ represents a hydrogen atom or a $C_1$-$C_5$ alkyl group, n is an integer of 1 to 5, m is an integer of 1 to 10 and l is 0 or an integer of 1 to 20;
$R_1$ represents a hydrogen atom, a $C_1$-$C_5$ alkyl group or an aryl group; and
X represents an oxygen atom, a sulfur atom, $-COO-$ or $-NR_5-$, in which $R_5$ is a hydrogen atom or a $C_1$-$C_5$ alkyl group, provided that if Y is present, X is not $-NR_5-$,
its production and polymers prepared therefrom.

7 Claims, No Drawings

POLYMERIZABLE COMPOUND AND POLYMER THEREFROM

FIELD OF THE INVENTION

The present invention relates to a polymerizable compound which has both an alpha-ketoester group and a polymerizable double bond, and a polymer prepared therefrom.

BACKGROUND OF THE INVENTION

It has been known that an alpha-ketoester group

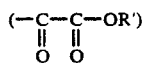

is a chemically active group which can be ester-exchanged with an active hydrogen containing-compound, such as an alcohol or an amine, or can be easily hydrolyzed.

If the alpha-ketoester group is introduced into a polymer, the polymer would be chemically interesting. In order to obtain such polymers, a compound which has both an alpha-ketoester group and a polymerizable double bond is required.

EP 20,000 B1 and NL 6612666 disclose number of a compounds which have both an alpha-ketoester group and a polymerizable double bond in the form of general formula, but actually synthetic examples are very few.

SUMMARY OF THE INVENTION

The present invention provides a novel compound which has both an alpha-ketoester group and a polymerizable double bond. The compound has the formula (I);

$$A-X-COCOOR_1 \quad (I)$$

wherein A represent a $C_1-C_{18}$ alkenyl, alkynyl, alkenylaryl or alkenylaralkyl group, or a group represented by:

(wherein $R_2$ and $R_3$, which is the same or different, represents a hydrogen atom, or a $C_1-C_5$ alkyl group, Y represents an oxygen atom or $-NR_4-$, in which $R_4$ represents a hydrogen atom or a $C_1-C_5$ alkyl group, n is an integer of 1 to 5, m is an integer of 1 to 10 and l is 0 or an integer of 1 to 20); $R_1$ represents a hydrogen atom, a $C_1-C_5$ alkyl group or an aryl group; and X represents an oxygen atom, a sulfur atom, $-COO-$ or $-NR_5-$, in which $R_5$ is a hydrogen atom or a $C_1-C_5$ alkyl group, provided that if the compound contains a Y group, X is not $-NR_5-$.

The present invention also provides a production of the above compound and polymers prepared therefrom.

The present invention further provides a curable composition which contains the polymer obtained from the above compound.

DETAILED DESCRIPTION OF THE INVENTION

The polymerizable compound of the present invention can be prepared by reacting an active hydrogen-containing compound represented the formula;

$$A-XH \quad (II)$$

wherein A and X are the same as defined above with an ester compound represented by the formula;

$$Z-COCOOR_1 \quad (III)$$

wherein $R_1$ is the same as defined above and Z represents a halogen atom or $-OR_1-$.

The active hydrogen-containing compound (II) is a compound which has a hydrogen atom directly bonded to an electrophilic atom or group (e.g. oxygen, sulfur, $-NR_4-$ or $-COO-$). Accordingly, the active hydrogen may be present in a hydroxyl group, a thiol group, an amino group or a carboxyl group. The group A in the active hydrogen-containing compound (II) is a group which imparts polymerizability to the compound, and includes a $C_1-C_{18}$ alkenyl group, such as propenyl, isopropenyl, butenyl, allyl etc.; a $C_1-C_{18}$ alkynyl, such as propynyl, butynyl etc.; a $C_1-C_{18}$ alkenylaryl group, such as vinylphenyl, propenylphenyl etc.; a $C_1-C_{18}$ alkenylaralkyl group, such as vinylphenylethyl, vinylphenylpropyl etc.; and a group represented by

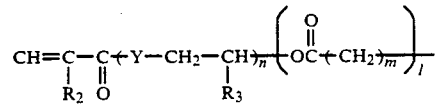

wherein $R_2$ and $R_3$, which is the same or different, represents a hydrogen atom, or a $C_1-C_5$ alkyl group, Y represents an oxygen atom or $-NR_4-$, in which $R_4$ represents a hydrogen atom or a $C_1-C_5$ alkyl group, n is an integer of 1 to 5, m is an integer of 1 to 10 and l is 0 or an integer of 1 to 20. Typical examples of the active hydrogen-containing compounds are acrylic acid, methacrylic acid, 2-hydroxyethyl methacrylate, allylamine, 2-hydroxyethyl acrylate, propargyl alcohol, 2-hydroxypropyl methacrylate, p-aminostyrene, 2-hydroxypropyl acrylate, p-hydroxyethylstyrene, allylamine, propargylamine, 2-(2-hydroxyethoxy)-ethyl acrylate, 2-hydroxy-3-(2-propenyloxy)-propylacrylate,

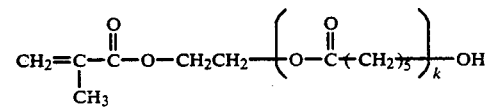

[k = 1 to 5]

and the like.

The ester compound (III) employed in the present invention includes oxalic diesters, such as dimethyl oxalate, diethyl oxalate, diisopropyl oxalate, dibutyl oxalate, diphenyl oxalate etc.; alkoxalyl halides, such as methoxalyl chloride, ethoxalyl chloride, etc.

If the ester compound (III) is the alkoxalyl halide (Z is halogen), the reaction between the compound (III) and the compound (II) is a dehydrohalogenation reaction which quantitatively progresses. The reaction may be carried out at room temperature to 150° C., preferably 50° to 100° C. in an inert solvent. Examples of the inert solvents are aliphatic hydrocarbons, such as pentane, hexane and heptane; aromatic hydrocarbons, such as benzene, toluene and xylene; cycloaliphatic hydrocarbons, such as cyclohexane, methylcyclohexane and decalin; petroleum hydrocarbons, such as petroleum ether and petroleum benzine; halogenated hydrocarbons, such as carbon tetrachloride, chloroform, 1,2-dichloroethane; ethers, such as ethyl ether, isopropyl ether, anisole, dioxane and tetrahydrofuran; ketones, such as acetone, methyl ethyl ketone, cyclohexanone, acetophenone and isophorone; esters, such as ethyl acetate, butyl acetate, propyleneglycol monoethyl ether acetate and ethyleneglycol monoethyl ether acetate; acetonitrile; dimethylformamide; dimethylsulfonide; and the like. Removal of the byproduct hydrogen chloride may be carried out by a method wherein nitrogen gas is blown into the reaction vessel, or a method wherein hydrogen chloride is reacted with a tertiary amine to form a salt of HCl which is removed out.

If the compound (III) is the oxalic diester (Z is $-OR_1$), the reaction compound between the compound (III) and the compound (II) is an ester exchange reaction which is generally carried out using excess dialkyl oxalate in the presence of a catalyst and a polymerization inhibitor. The amount of the dialkyl oxalate is 2 to 20 times, preferably 3 to 8 times larger than the molar amount of the compound (II) and the reaction temperature is within the range of room temperature to 150° C., preferably 50° to 120° C. The reaction may be carried out in an inert solvent as mentioned above. Typical examples of the catalysts are tin compounds, such as dibutyltin dilaurate, dibutyltin oxide and monobutyltin triheptate; mixture catalysts, such as dimethyltin diiodide and tetraphenylantimony iodide, dimethyltin diiodide and hexamethyl phosphoric triamide; acidic compounds, such as p-toluenesulfonic acid, dodecylbenzenesulfonic acid, sulfuric acid, chloric acid, nitric acid and boron trichloride etherate; basic compounds, such as triethylamine, 1,4-diazabicyclo[2,2,2]octane, 1,8-diazabicyclo[5,4,0]undecene-b 7, pyridine sodium methoxide, sodium ethoxide and t-butoxypotassium hexamethylphosphoric triamide, metal oxides or metal salts, such as manganese acetate, cobalt acetate, calcium acetate, lithium acetate, zinc acetate, magnesium acetate, antimony trioxide, lead dioxide, ferric chloride, aluminum triisopropoxide and tetraisopropoxy titanium; and the like. Typical examples of the polymerization inhibitors are hydroquinone, p-methoxyphenol, 2,6-di-t-butyl-4-methylphenol, 4-t-butylcatechol, bisdihyroxybenzylbenzene, 2,2'-methylenebis(6-t-butyl-3-methylphenol), 4,4'-thiobis(6-t-3-methylphenol), p-nitrosophenol, diisopropylxanthogen sulfide, N-nitrosophenylhydroxylamine ammonium salt, dithiobenzylsulfide, p,p'-ditolyltrisulfide, p,p'-ditolyltetrasulfide, dibenzyltetrasulfide, tetraethylthiuramsulfide and the like.

The obtained product may be purified by distillation, crystallization, etc. Distillation is generally effected at a reduced pressure (from atmospheric pressure to 0.01 mmHg) at a temperature of room temperature to 180° C., preferably 50° to 120° C. in the presence of zeolite or with stirring.

The obtained polymerizable compound of the present invention can be polymerized solely or with a copolymerizable compound. Polymerization may be carried out at a temperature of 50° to 150° C., preferably 70° to 120° C., in the inert solvent mentioned above in the presence of a polymerization initiator. Typical examples of the polymerization initiators are azobisisobutylonitrile, benzoyl peroxide, cumene hydroperoxide, tetramethyltiuramdisulfide, 2,2-azobis(4-methoxy-2,4-dimethylvaleronitrile, acetylcyclohexylsulfonyl peroxide, 2,2'-azobis(2,4-dimethylvaleronitrile) and the like.

The copolymerizable compound employed in the present invention includes mono-olefins or di-olefins, such as styrene, alpha-methylstyrene, alpha-ethylstyrene, 2-methyl-1-butene, ethylene, propylene, butylene, amylene, hexylene, butadiene-1,3, isoprene etc.; halogenated mono-olefins or di-olefins, such as alpha-chlorostyrene, alpha-buromostyrene etc.; organic or inorganic esters, such as vinyl acetate, vinyl propionate, vinyl butylate, vinyl banzoate, methyl methacrylate, ethyl methacrylate, propyl methacrylate, hexyl methacrylate, methyl acrylate, ethyl acrylate, propyl acrylate, allyl chloride, allylcyanamide, allyl acetate, allyl propionate, allyl butylate, dimethyl maleate, diethyl maleate, dimethyl fumarate, diethyl fumarate, dimethacryl fumarate, diethyl glutarate etc.; organic nitriles, such as acrylonitrile, methacrylonitrile, ethacrylonitrile, 3-octenenitrile, crotonitrile and oleonitrile; unsaturated acids, such as acrylic acid, methacrylic acid, crotonic acid etc.; unsaturated alcohols, such as a monoester of the unsaturated acid mentioned above and a glycol (e.g. ethylene glycol or propylene glycol); unsaturated amides, such as acrylamide, methacrylamide, crotonamide etc.; unsaturated sulfonic acids or salts thereof, such as 2-sulfoethyl acrylate, p-vinylbenzenesulfonic acid etc.

The polymer (or copolymer) of the present invention has at least two alpha-ketoester groups which are reactive with other active hydrogen-containing groups, particularly a hydroxyl group. Accordingly, the polymer may be combined with a compound having at least two hydroxyl groups, i.e. polyhydroxyl compound, to form a curable composition. The curable composition has excellent properties in low temperature curing ability and acid resistance. The polyhydroxyl compound includes polyhydric alcohols, polyester polyols, polyether polyols, polyurethane polyols, polyvinyl alcohols, phenol resins, hydroxyl-containing polybutadine, hydroxy-containing polychloroprene, ring-opened epoxy resins, polyorganosiloxane and the like.

Typical examples of the polyhydric alcohols are 3-allyloxy-1,2-propane diol, 2,2-bis(chloromethyl)-1,3-propane diol, 2-bromo-2-nitro-1,3-propane diol, 3-bromo-1,2-propane diol, butane diol, butyne diol, cyclohexane diol, cyclooctane diol, cyclopentane diol, decalin diol, decane diol, ethylene glycol, propylene glycol, dihydroxyacetophenone, dihydroxyanthraquinone, dihydroxybenzophenone, hydroxybenzylalcohol, catechol, pentaerythritol, glycerol, amylose, lactose, sucrose, manitol, maltose and the like.

The acryl polyol is a polymer of a hydroxyl containing ethylenically unsaturated monomer. Examples of the hydroxy containing unsaturated monomers are 2-hydroxyethyl (meth)acrylate, 2-hydroxypropyl (meth)acrylate, 2-hydroxybutyl (meth)acrylate and the like. The acryl polyol may be a copolymer of the above mentioned monomers with other monomers. Examples of the other monomers are methyl (meth)acrylate, ethyl (meth)acrylate, n-butyl (meth)acrylate, isobutyl (meth)acrylate, ethylhexyl (meth)acrylate, alpha-methylstyrene, vinyltoluene, t-butylstyrene, ethylene, propylene, vinyl acetate, vinyl propionate, acrylonitrile, methacrylonitrile, dimethylaminoethyl (meth)acrylate, and the like.

Typical examples of the polyester polyols are a condensate of a polyhydric alcohol as mentioned above and a polybasic acid or an anhydride thereof (e.g. phthalic acid, tetrahydrophthalic acid, tetrachlorophthalic acid, hexahydrophthalic acid, succinic acid, maleic acid, fumaric acid, adipic acid, sebacic acid, trimellitic acid, pyromellitic acid etc.); a reaction product of a polyhydric alcohol as mentioned above with an epoxy compound (e.g. n-butyl glycidyl ether, allyl glycidyl ether, Cardura E available from Yuka Shell Company etc.); an alkyd polyol (a product of a polyhydric alcohol and oil (e.g. soybean oil and safflower oil)); a ring open product of ε-caprolantone; and the like.

Examples of the polyether polyols are an adduct of a polyhydric alcohol as mentioned above and an alkylene oxide (e.g. ethylene oxide, propylene oxide, tetrahydrofuran etch) and the like.

The polyurethane polyol may be prepared by reacting a polyol as mentioned above and a polyisocyanate compound. Examples of the polyisocyanate compounds are ethylene diisocyanate, propylene diisocyanate, tetramethylene diisocyanate, hexamethylene diisocyanate, 1-methyl-2,4-diisocyanatocyclohexane, 1-methyl-2,6-diisocyanatocyclohexane, diisocyanatodimethylxylene, diisocyanatodiethylxylene, lysine diisocyanate, 4,4'-methylenebis(cyclohexylisocyanate), α 4,4'-ethylenebis(cyclohexylisocyanate), alpha, alpha'-diisocyanato-1,3-dimethylbenzene, alpha, alpha'-diisocyanato-1,4-dimethylbenzene, isophorone diisocyanate, 2,4-tolylene diisocyanate, 2,6-tolylene diisocyanate, 1,5-naphthylene diisocyanate, 4,4'-methylenebis(-phenyleneisocyanate), triphenylmethane triisocyanate and a polymer thereof. The polyol for the polyurethane polyol may be polymeric polyol, such as polyether polyol or polyester polyol.

Examples of the phenol resins are novolac or resol type phenol resin, rosin modified phenol resin, alkylphenol resin, butylated resol resin, allyl ether resol resin and the like.

The polyorganosiloxane polyol includes a polymer or cyclic compound having both alkylhydroxyalkylsiloxy unit and dialkylsiloxy unit or(and) diphenylsiloxy unit, α,ω-bis(hydroxyalkyl)polydimethylsiloxane and the like. Typical examples of the polyols are

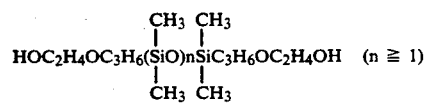

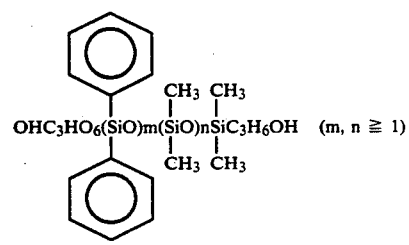

-continued

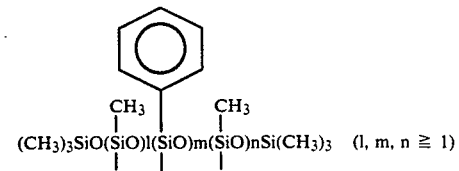

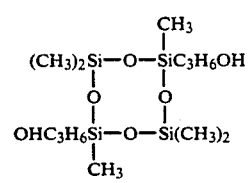

The curable composition of the present invention may generally contain a catalyst as mentioned in the synthesis of the polymerizable compound. The catalyst may be present in the composition in an amount of 0.0001 to 10% by weight, preferably 0.001 to 5% by weight based on the total amount of the poly(alpha-ketoester) and the polyhydroxyl compound.

The curable composition may contain a solvent is necessary. The solvent can be the inert solvent as mentioned above, but alcohols (e.g. ethylene glycol, 2-ethylhexanol, t-butanol, n-hexanol, n-butanol, cyclohexanol, isopropanol, n-propanol, benzyl alcohol, ethanol, methanol etc.) may be employed. The solvent may be present in the composition in an amount of 0.01 to 90% by weight, preferably 0.5 to 80% by weight, but alcohols are preferably 50% by weight or less because they are ester-exchanged with alkoxalyl ester.

The curable composition may be cured at a temperature of 70° to 200° C., preferably 90° to 180° C. for 5 minutes to 2 hours, preferably 10 minutes to one hour.

The polymerizable compound and polymer of the present invention have the alpha-ketoester group which can be ester-exchanged with an active hydrogen containing-compound, such as an alcohol or an amine, or can be easily hydrolyzed. The polymer may be suitable for coating, adhesive, plastics, fiber and the like. The polymer may be combined with another active hydrogen containing compound to form a curable composition. The composition is suitable for the field of coating or adhesive.

EXAMPLES

The present invention is illustrated by the following Examples which, however, are not to be construed as limiting the present invention to their details.

EXAMPLE 1

A solution of 5.80 g (0.1 mol) of allyl alcohol and 150 ml of benzene was mixed with 10.1 g (0.1 mol) of triethylamine, and cooled to 8° C. A solution of 13.65 g (0.1 mol) of ethoxalyl chloride and 100 ml of benzene was added dropwise for 40 minutes. The formed triethylamine hydrochloric salt was filtered at a reduced pressure and rinsed with 50 ml of benzene. The filtrate was condensed at a reduced pressure to obtain brown liquid which was Kugel-rohr distilled to obtain transparent liquid of allylethyl oxalate. It has a boiling point of 93° to 95° C./0.25 Torr (using Glass Tube Oven available from Shibata Kagaku Co., Ltd.) and a viscosity of 30 cp (using EL type viscometer available from Tokyo Keiki Co., Ltd. at 25° C.).

EXAMPLES 2 TO 8

Synthesis was conducted as generally described in Example 1, with the exception that reactants and conditions were those shown in Table 1. The viscosity or melting point of the obtained compound is shown in Table 1.

TABLE 1

| Example No. | Compound (II) | Compound (III) | Kugel-roll boiling point | Viscosity[1] or melting point (°C.) |
|---|---|---|---|---|
| 2 | Propargyl alcohol | Ethoxalyl chloride | 168–166° C./0.3 Torr | 100 cp |
| 3 | Methacrylic acid | Ethoxalyl chloride | 122–124° C./0.3–0.2 Torr | 57 cp |
| 4 | 2-Hydroxyethyl methacrylate | Ethoxalyl chloride | 124° C./0.4 Torr | 200 cp |
| 5 | 2-Hydroxyethyl acrylate | Ethoxalyl chloride | — | 250 cp |
| 6 | Allylamine | Ethoxalyl chloride | 133–124° C./0.3 Torr | — |
| 7 | Propargylamine | Ethoxalyl chloride | 152–153° C./0.5–0.6 Torr | 61–63° C. |
| 8 | FM-2[2] | Ethoxalyl chloride | — | 77 cp |

[1]Measure at 25° C.
[2]$CH_2=C(CH_3)-COO-CH_2CH_2-O(CO-(CH_2)_5O)_2H$ available from Daicel Chemical Industries Co., Ltd.

EXAMPLE 9

Three grams of p-toluenesulfonic acid and 58.0 g (1 mol) of allyl alcohol were mixed with 438 g (3 mol) of diethyl oxalate and mixed at 90° C. for 5 hours with distilling ethanol. It was cooled and then distilled at a reduced pressure to obtain allylethyl oxalate.

EXAMPLE 10

Ethylpropargyl oxalate was obtained as generally described in Example 9, with the exception that 50 g (1 mol) of propargyl alcohol, 438 g (3 mol) of diethyl oxalate and 3 g of p-toluenesulfonic acid were employed.

EXAMPLE 11

Ethylmethacryloyl oxalate was obtained as generally described in Example 9, with the exception that 86 g (1 mol) of methacrylic acid, 438 g (3 mol) of diethyl oxalate and 3 g of p-toluenesulfonic acid were employed.

EXAMPLE 12

2-Ethoxalyloxyethyl methacrylate was obtained as generally described in Example 9, with the exception that 130 g (1 mol) of 2-hydroxyethyl methacrylate, 438 g (3 mol) of diethyl oxalate and 3 g of p-toluenesulfonic acid were employed.

EXAMPLE 13

2-Ethoxalyloxyethyl acrylate was obtained as generally described in Example 9, with the exception that 116 g (1 mol) of 2-hydroxyethyl acrylate, 438 g (3 mol) of diethyl oxalate and 3 g of p-toluenesulfonic acid were employed.

EXAMPLE 14

A solution of 57.0 g (1 mol) of allylamine and 200 ml of tetrahydrofuran was added dropwise to 146 g (1 mol) of diethyl oxalate with cooling by water. After the completion of the addition, the reaction mixture was condensed at a reduced pressure and then distilled under vacuum to obtain N-allylethyl oxalate.

EXAMPLE 15

N-Propargylethyl oxalate was obtained as generally described in Example 14, with the exception that 56 g (1 mol) of propargylamine and 146 g (1 mol) of diethyl oxalate were employed.

EXAMPLE 16

A 500 ml flask equipped with a decanter, a thermometer, a stirrer and an inlet for nitrogen gas was charged with 65.1 g (0.5 mol) of 2-hydroxyethyl methacrylate and 365.4 g (2.5 mol) of diethyl oxalate, to which 2 g (10 mmol) of p-toluenesulfonic acid (catalyst) and 4 g of hydroquinone (polymerization inhibitor) were added. The mixture was heated to keep 120° C. for 4 hours in nitrogen atmosphere with distilling 14 mol (0.25 mol) of ethanol away. The reaction mixture was evaporated to remove excess diethyl oxalate and then distilled under vacuum to obtain 88.1 g (yield 76.5%) of 2-ethoxalyloxyethyl methacrylate (colorless transparent liquid) (bp 98° C./0.3 mmHg).

EXAMPLE 17

A 500 ml flask equipped with a decanter, a thermometer, a stirrer and an inlet for nitrogen gas was charged with 65.1 g (0.5 mol) of 2-hydroxyethyl methacrylate and 365.4 g (2.5 mol) of diethyl oxalate, to which 2 g (10 mmol) of p-toluenesulfonic acid (catalyst) and 4 g of 2-t-butylhydroquinone (polymerization inhibitor) were added. The mixture was heated to keep about 130° C. for 3 hours in nitrogen atmosphere with distilling 22 ml (0.38 mol) of ethanol away. The reaction mixture was evaporated to remove excess diethyl oxalate and then distilled under vacuum to obtain 64.8 g (yield 76.5%) of 2-ethoxalyloxyethyl methacrylate (by 84°–125° C./0.4 mmHg).

EXAMPLE 18

A 500 ml flask equipped with a decanter, a thermometer, a stirrer and an inlet for nitrogen gas was charged with 65.1 g (0.5 mol) of 2-hydroxyethyl methacrylate and 365.4 g (2.5 mol) of diethyl oxalate, to which 2 g (10 mmol) of p-toluenesulfonic acid (catalyst) and 4 g of 2,5-di-t-butylhydroquinone (polymerization inhibitor) were added. The mixture was heated to keep about 130° C. for 3 hours in nitrogen atmosphere with distilling 23.5 ml (0.40 mol) of ethanol away. The reaction mixture was evaporated to remove excess diethyl oxalate and then distilled under vacuum to obtain 64.8 g (yield 52.4% of 2-ethoxalyloxyethyl methacrylate (bp 95°-125° C./0.3 mmHg).

EXAMPLE 19

A 500 ml flask equipped with a decanter, a thermometer, a stirrer and an inlet for nitrogen gas was charged with 65.1 g (0.5 mol) of 2-hydroxyethyl methacrylate and 365.4 g (2.5 mol) of diethyl oxalate, to which 2 g (10 mmol) of dibutyltin dilaurate (catalyst) and 4 g ob 2,5-di-t-butylhydroquinone (polymerization inhibitor) were added. The mixture was heated to keep it at about 120° C. for 2 hours in nitrogen atmosphere with distilling 32.5 ml (0.56 mol) of ethanol away. The reaction mixture was evaporated to remove excess diethyl oxalate and then distilled under vacuum to obtain 84.2 g (yield 73.2%) of 2-ethoxalyloxyethyl methacrylate (bp 124° C./0.4 mmHg).

EXAMPLE 20

Preparation of p-Ethoxalyloxyethylstyrene

A 200 ml flask equipped with a stirrer, a thermometer and a dropping funnel was charged with 14.8 g (0.1 mol) of p-hydroxyethylstyrene, 150 ml of benzene and 10.1 g (0.1 mol) of triethylamine and cooled to 10° C. To the mixture was added dropwise with stirring 13.7 g (0.1 mol) of ethoxalyl chloride for one hour at 10° C. to precipitate a hydrochloride of triethylamine (white solid). After mixing at room temperature for 2 hours, 80 g of hexane was added to complete precipitation of the hydrochloride. The hydrochloride is removed by filteration and the resultant filtrate was condensed to obtain the aimed compound. The compound was identified by $^1$H NMR (360 Mz) and IR.

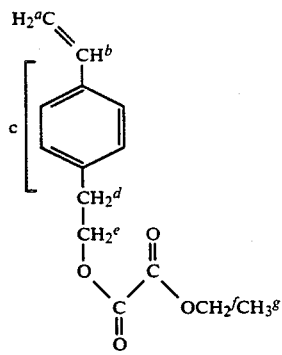

$^1$H-NMR: g, 1.4 (3H,t), d; 3.1 (2H,t), f; 4.4 (2H,q), e; 4.5 (2H,t), a; 5.25-5.75 (2H,dd), b; 6.75 (1H,dd), c; 7.2-7.5 (4H,m).

| IR (cm$^{-1}$) | |
|---|---|
| 2980 | (CH) |
| 1740, 1760 | (C=O) |
| 1625 | (C=C) |
| 1515, 1460 | 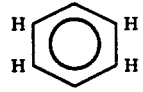 |

EXAMPLE 21

A 200 ml flask equipped with a decanter, a condenser, a stirrer and a dropping funnel was charged with 50 g of butyl acetate and heated to 100° C. To the content was added dropwise 30.75 g of 2-ethoxalyloxyethyl methacrylate, 35.69 g of methyl methacrylate, 21.92 g of n-butyl acrylate and 1.33 g of azobisisobutylonitrile for 2 hours. After mixing for 30 minutes, 0.88 g of azobisisobutylonitrile and 17.8 g of butyl acetate were added dropwise for 30 minutes. It was mixed with heating for 1.5 hours and cooled to obtain transparent and light yellow polymer (Mn=14,200, Mw=37,500, α=2.63).

EXAMPLE 22

A 200 ml flask equipped with a decanter, a condenser, a stirrer and a dropping funnel was charged with 70 g of butyl acetate and 20 g of butanol, and heated to 110° C. To the content was added dropwise 16.4 g of 2-ethoxalyloxyethyl methacrylate, 50.0 g of methyl methacrylate, 24.3 g of n-butyl acrylate, 9.3 g hydroxyethyl methacrylate and 1.5 g of azobisisobutylonitrile for 3 hours. After mixing for 30 minutes, 0.5 g of azobisisobutylonitrile and 10.0 g of butyl acetate were added dropwise for 30 minutes. It was mixed with heating for 1.5 hours and cooled to obtain transparent and light yellow polymer (Mn=9,730, Mw=30,942, α=3.17).

EXAMPLE 23

A 200 ml flask equipped with a decanter, a condenser, a stirrer and a dropping funnel was charged with 42.9 g of xylene and 1 g of Kaya Ester-O (t-butylperoxy-2-ethylhexanoate available from Akzo Chemical Company), and heated to 140° C. To the content was added dropwise 41.0 g of 2-ethoxalyloxyethyl methacrylate, 40.0 g of methyl methacrylate, 19.0 g of n-butyl acrylate and 4.0 g of azobisisobutylonitrile for 2 hours. After mixing for 30 minutes, 10.0 g of xylene was added dropwise for 30 minutes. It was mixed with heating for 1.5 hours and cooled to obtain transparent and light yellow polymer (Mn=2,799, Mw=5,695, α=2.03).

EXAMPLE 24

A 200 ml flask equipped with a decanter, a condenser, a stirrer and a dropping funnel was charged with 27.0 g of butyl acetate and heated to 110° C. To the content was added dropwise 30.0 g of 2-ethoxalyloxyethyl methacrylate and 0.45 g of azobisisobutylonitrile. After mixing for 30 minutes, 0.15 g of azobisisobutylonitrile and 3.0 g of butyl acetate were added dropwise for 30 minutes. It was mixed with heating for 1.5 hours and cooled to obtain transparent and light yellow polymer (Mn=8,050, Mw=17,240, α=2.14).

EXAMPLE 25

A 100 ml flask equipped with a decanter, a condenser, a stirrer and a dropping funnel was charged with 13.1 g of xylene and heated to 120° C. A mixture of 33.8 g of the product of Example 8, 3.8 g of Kaya Ester-O, 3.8 g of alpha-methylstyrene dimer and 3.8 g of xylene was added dropwise for 3 hours. After mixing for 30 minutes, 0.38 g of Kaya Ester and 3.3 g of xylene were added dropwise for one hour. It was mixed with heating for 1.5 hours and cooled to obtain transparent and light yellow liquid (Viscosity=253 cp).

EXAMPLE 26

A 100 ml flask equipped with a decanter, a condenser, a stirrer and a dropping funnel was charged with 15.0 g of xylene and heated to 130° C. A mixture of 32.7 g of the product of Example 8, 9.3 g of 2-hydroxyethyl methacrylate, 2.5 g of butanol, 3.1 g of n-butyl methacrylate, 4.5 g of Kaya Ester-O and 5.0 g of alpha-methylstyrene dimer was added dropwise for 3 hours. After mixing for 30 minutes, 0.38 g of Kaya Ester and 3.3 g of xylene were added dropwise for one hour. It was mixed with heating for 1.5 hours and cooled to obtain transparent and light yellow liquid ( Viscosity=99.2 cp, nonvolatile content=60.4%).

EXAMPLE 27

A 100 ml flask equipped with a decanter, a condenser, a stirrer and a dropping funnel was charged with 15.0 g of xylene and heated to 130° C. A mixture of 24.5 g of the product of Example 8, 19.2 g of FM-2, 1.35 g of n-butyl methacrylate, 5 g of alpha-methylstyrene dimer, 2.5 g of butanol and 4.5 g of Kaya Ester-O was added dropwise for 3 hours. After mixing for 30 minutes, 0.5 g of Kaya Ester and 5.0 g of xylene were added dropwise for one hour. It was mixed with heating for 1.5 hours and cooled to obtain transparent and light yellow liquid (Viscosity=74.4 cp, nonvolatile content=63.4%).

EXAMPLES 28 TO 33

A 200 ml of flask equipped with a decanter, a condenser, a stirrer and a dropping funnel was charged with 21.8 g of xylene and heated to 135° C. To the content, 62.5 g of a monomer mixture shown in Table 2, 6.3 g of Kaya Ester-O and 6.3 g of xylene were added dropwise for 3 hours. After mixing for 30 minutes, 0.63 g of Kaya Ester and 5.0 g of xylene were added dropwise for one hour. It was mixed with heating for 1.5 hours and heated to remove 15 g of xylene. It was then cooled to obtain transparent and light yellow liquid. The liquid had physical properties as shown in Table 2.

TABLE 2

| Example No. | Momomer mixture | Nonvolatile content[1] | Viscosity[2] (cps) |
|---|---|---|---|
| 28 | EOMA[3]/MSD[4] = 90/10 | 79 | 1229 |
| 29 | EOFM-2[5]/MSD = 90/10 | 80 | 211 |
| 30 | EOMA/MMA[6]/MSD = 55.4/34.6/10 | 78 | 410 |
| 31 | EOMA/MMA/MSD = 85/5/10 | 76 | 4429 |
| 32 | EOMA/ST[7]/MSD = 46.3/43.7/10 | 81 | 5760 |
| 33 | EOMA/EHA[8]/MSD = 73.8/16.2/10 | 76 | 550 |

[1]The obtained polymer solution was heated at 130° C. for 30 minutes. The weight after heating the solution was divided by the weight before heating. The obtained value times 100 is shown in Table 2.
[2]Measured by an E type viscometer at 25° C.
[3]2-Ethyloxalyloxy methacrylate
[4]Alpha-methylstyrene dimer
[5]An ethoxalylated FM-2 (a compound of 2-hydroxyethyl methacrylate ring-opened with average two epsilon-caprolantone molecules; available from Daicel Chemical Industries Co., Ltd.)
[6]Methyl methacrylate
[7]Styrene

PRODUCT EXAMPLE 1

Acryl Polyol

A one liter flask equipped with a decanter, a condenser, a stirrer and a dropping funnel was charged with 180.0 g of butyl acetate and heated to 120° C. A mixture of 142.7 g of methyl methacrylate, 87.7 g of n-butyl acrylate, 69.6 g of 2-hydroxyethyl methacrylate and 4.5 g (1.5 wt %/monomers) of azobisisobutylonitrile was added dropwise for 3 hours. After mixing for 30 minutes, 1.5 g (0.5 wt %/monomers) of azobisisobutylonitrile and 30.0 g of butyl acetate were added dropwise for 30 minutes. It was mixed with heating for 1.5 hours and cooled to obtain transparent and light yellow polymer (Mn=8,870, Mw=20,600 OH value=100, α=2.31).

PRODUCTION EXAMPLE 2

Acryl Polyol

A 200 ml flask equipped with a decanter, a condenser, a stirrer and a dropping funnel was charged with 21.8 g of xylene and heated to 135° C. To the content, 62.5 g of a monomer mixture (FM-2/styrene/isobutyl methacrylate/alpha-methylstyrene dimer=55.2/10.2/27.4/10.2), 6.3 g of Kaya Ester-O and 6.3 g of xylene were added dropwise for 3 hours. After mixing for 30 minutes, 0.63 g of Kaya Ester-O and 5.0 g of xylene were added dropwise for one hours. After mixing with heating for 1.5 hours, it was heated to remove 15 g of xylene. The obtained solution was cooled to room temperature to obtain transparent and light yellow polymer. The polymer solution has a viscosity of 326 (E type viscometer at 25° C.) and a nonvolatile content of 70% (130° C., 30 minutes).

EXAMPLE 34

One of the products (curing agent) prepared in Examples 28 to 33 and the acryl polyol of Production Example 2 were mixed with 1 wt %/solid content of dibutyltin dilaurate. The resultant composition was coated on a tin plate by a bar coater No. 40, and then baked at 130° or 150° C. for 30 minutes. Curing properties were evaluated and the results where shown in Table 3.

TABLE 3

| Curing agent (weight) | Amount of the polyol | Acetone rubbing test[9] 130° C. | 150° C. |
|---|---|---|---|
| Ex. 28 (1.49 g) | 4.04 g | 11 | 19 |
| Ex. 29 (2.26 g) | 3.00 g | 9 | 1 |
| Ex. 30 (2.02 g) | 3.43 g | 10 | 16 |
| Ex. 31 (1.44 g) | 3.76 g | 7 | 9 |
| Ex. 32 (2.22 g) | 3.15 g | 10 | 15 |
| Ex. 33 (1.71 g) | 3.81 g | 9 | 10 |

[9]A piece of cloth which was saturated with acetone was wrapped on a finger and rubbed on the cured coating. Number of rubbing until the coating is peeled off is shown in Table 3.

EXAMPLE 35

A catalyst was mixed with 8.51 g of the 2-ethoxalyloxy methacrylate copolymer prepared in Example 21 and 6.49 g of the acryl polyol of Production Example 1 in an amount ratio of catalyst/resin solid content of 1 wt % to form a resin composition. The catalyst was selected from dibutyltin dilaurate (DBTL), diazabicyclooctane (DABCO) and p-toluenesulfonic acid monohydrate (PTS). Also, another resin composition which did not contain any catalyst was prepared. The resin composition was coated on a tin plate by a bar coater in a thickness of 20 microns, and then baked at 110°, 130°, 150° or 180° C. for 30 minutes. Curing properties were evaluated and the results were shown in Table 4.

TABLE 4

| Curing temp. | Number[10] | Catalyst | Acetone rubbing[9] | Gellation %[11] | Pencil hardness[12] |
|---|---|---|---|---|---|
| 110° C. | 1 | Nothing | — | — | |
| | 2 | | | | |
| | 1 | DBTL | 5 | 85.8 | H |
| | 2 | | | 81.8 | H |
| | 1 | DABCO | 5 | 64.6 | H |
| | 2 | | | 69.8 | H |

TABLE 4-continued

| Curing temp. | Number[10] | Catalyst | Acetone rubbing[9] | Gellation %[11] | Pencil hardness[12] |
|---|---|---|---|---|---|
| | 1 | PTS | — | — | |
| | 2 | | | | |
| 130° C. | 1 | Nothing | — | — | |
| | 2 | | | | |
| | 1 | DBTL | 16 | 95.1 | H |
| | 2 | | | 96.6 | H |
| | 1 | DABCO | 5 | 84.4 | H |
| | 2 | | | 83.2 | H |
| | 1 | PTS | — | — | |
| | 2 | | | | |
| 150° C. | 1 | Nothing | 5 | 3.8 | 2H |
| | 2 | | | 2.2 | |
| | 1 | DBTL | 50 | 99.5 | 2H |
| | 2 | | | 99.6 | 2H |
| | 1 | DABCO | 34 | 89.1 | 2H |
| | 2 | | | 87.3 | |
| | 1 | PTS | 13 | 19.3 | 2H |
| | 2 | | | 19.3 | 2H |
| 180° C. | 1 | Nothing | 6 | 5.8 | 2H |
| | 2 | | | 5.1 | 2H |
| | 1 | DBTL | 50 or more | 99.7 | 2H |
| | 2 | | | 99.6 | 2H |
| | 1 | DABCO | 50 or more | 89.8 | 2H |
| | 2 | | | 89.4 | 2H |
| | 1 | PTS | 10 | 76.6 | 2H |
| | 2 | | | 77.0 | 2H |

[10] Number of times of test.
[11] Gellation %; The coated film was placed in a acetone refluxing condition for three hours and then dried at 60° C. for 5 hours. The remaining film is expressed with percentage.
[12] Pencil hardness; the cured coating was scratched by pencils and was expressed by a hardness of a pencil when the coating was defected.

EXAMPLES 36 TO 38

A 200 ml flask equipped with a decanter, a condenser, a stirrer and a dropping funnel was charged with xylene and n-butanol in an amount shown in the initial charge column of Table 5 and heated to a polymerization temperature. To the content, a monomer mixture shown in Table 5 and Kaya Ester-O were were added dropwise for 3 hours. After mixing for 5 hours, Kaya Ester-O and xylene were added dropwise in amounts shown in the after shot column of Table 5 for one hour. After mixing for 1.5 hours with heating, it was cooled to room temperature. The obtained polymer solution was transparent and light yellow. Its molecular weight, nonvolatile content and viscosity are shown in Table 6.

EXAMPLE 39

One of the resins of Examples 36 to 38 was mixed with an amount of 1 wt %/resin solid content of dibutyltin dilaurate to form a resin composition. The resultant composition was coated on a tin plate by a bar coater No. 40, and then baked at 130° or 150° C. for 30 minutes. Curing properties were evaluated and the results were shown in Table 7.

TABLE 7

| | Acetone rubbing test | | Pencil hardness | |
|---|---|---|---|---|
| Resin No. | 130° C. | 150° C. | 130° C. | 150° C. |
| Ex. 36 | 25 | 38 | 2B | HB |
| Ex. 37 | 38 | 50 or more | HB | HB |
| Ex. 38 | 28 | 40 | HB | HB |

EXAMPLE 40

A 200 ml flask equipped with a decanter, a condenser, a stirrer and a dropping funnel was charged with 40 g of xylene and heated to 120° C. To the content, 200 g of a monomer mixture (FM-2/2-ethoxalyloxyethyl methacrylate/isobutyl methacrylate/alpha-methylstyrene dimer=51/32.8/10/6.2) and 9 g of Kaya Ester-O were added dropwise for 3 hours. After mixing for 30 minutes, 1 g of Kaya Ester-O and 10 g of xylene were added dropwise for one hour. After mixing with heating for 1.5 hours, it was heated to remove 30 g of xylene. The obtained solution was cooled to room temperature to obtain transparent and light yellow polymer. The polymer solution had a viscosity of 416 cps (E type viscometer at 25° C.) and a nonvolatile content at 70% (130° C., 30 minutes).

EXAMPLE 41

The resin of Example 40 was mixed with an amount of 1 wt %/resin solid content of a catalyst shown in Table 8. The resultant composition was coated on a tin plate by a bar coater No. 40, and then baked at 130° or 150° C. for 30 minutes. Curing properties were evaluated and the results were shown in Table 8.

TABLE 5

| Example No. | Monomer mixture (g) | | | | | | | Initiator (g) Kaya EsterO | Initial charge (g) | | After shot (g) | | Polymerization temperature (°C.) |
|---|---|---|---|---|---|---|---|---|---|---|---|---|---|
| | EOMA | HEMA | HEA | FM-1 | ST | EHMA | MSD | | XL | n-BuOH | Kaya EsterO | XL | |
| 36 | 24.88 | 4.92 | 4.93 | 7.92 | 2.39 | 10.66 | 6.06 | 6.06 | 18.18 | 9.09 | 0.61 | 4.85 | 120–125 |
| 37 | 25.82 | 5.11 | 4.55 | 8.21 | 6.29 | 3.47 | 6.29 | 6.29 | 18.87 | 6.29 | 0.63 | 5.03 | 130–135 |
| 38 | 20.66 | 4.09 | 3.64 | 6.57 | 6.29 | 9.06 | 6.29 | 6.29 | 18.87 | 6.29 | 0.63 | 5.03 | 130–135 |

EOMA; 2-ethoxalyloxyethyl methacrylate HEMA; 2-hydroxyethyl methacrylate HEA; 2-hydroxyethyl acrylate ST; styrene EHMA; 2-ethylhexyl methacrylate MSD; alpha-methylstyrene dimer XL; xylene n-BuOH; n-butanol

TABLE 6

| Example No. | Number average molecular weight ($\alpha$[13]) | Nonvolatile content | Viscosity[14] |
|---|---|---|---|
| 36 | 1771 (2.08) | 67.4 | C |
| 37 | 1866 (2.18) | 65.7 | J-K |
| 38 | 1866 (2.08) | 72.6 | S-T |

[13] Weight average molecular weight divided by number average molecular weight.
[14] Gardner-Holdt tube viscometer at 25° C.

TABLE 8

| | | Acetone rubbing test | |
|---|---|---|---|
| Number | Catalyst | 130° C. | 150° C. |
| 1 | Dibutyltin dilaurate | 23 | 42 |
| 2 | Dibutyltin dichloride | 12 | 38 |
| 3 | $(CH_3)SnI_2/(C_6H_5)_4SbI$ | 0 | 38 |
| 4 | $(CH_3)SnI_2/(MoN)_3PO$ | 7 | 38 |
| 5 | $H_2SO_4$ | 40 | 50 or more |
| 6 | $BF_3(Et2O)$ | 3 | 50 or more |
| 7 | 1.8-Diazabicyclo[5,4,0]undecene | 19 | 38 |
| 8 | 1,4-Diazabicyclo[2,2,2]octane | 2 | 30 |

TABLE 8-continued

| Number | Catalyst | Acetone rubbing test 130° C. | 150° C. |
|---|---|---|---|
| 9 | FeCl$_3$ | 8 | 50 |
| 10 | Al(i-PrO)$_3$ | 10 | 15 |
| 11 | Ti(i-PrO)$_4$ | 4 | 5 |
| 12 | Diacetyltetra-butyl stannoic acid | 25 | 40 |

EXAMPLE 42

A mixture was prepared by dissolving 52.1 g (0.4 mol) of hydroxyethyl methacrylate and 40.5 g (0.4 mol) of triethylamine in 250 ml of benzene and cooled to 2° C. To the content, a solution of 65.8 g (0.4 mol) of t-butoxalyl chloride in 200 ml of benzene was added dropwise for 3 hours while precipitating salt. After the completion of dropping, it was allowed to stand for 30 minutes without cooling to terminate reaction. The precipitated salt was filtered off and the filtrate was evaporated to obtain 99.9 g (yield 91%) of yellow liquid which was identified by IR and $^1$H-NMR to find t-butoxalyloxylethyl methacrylate.

IR (cm$^{-1}$, neat): 2950 (C—H), 1760-1720 (C=O), 1640 (C=O).

$^1$H-NMR (ppm, in CDCl$_3$, TMS Standard) e; 1.56 s,9H), c; 1.95 (s,3H), d; 4.46 (m,4H), a or b; 5.60 (s,1H), a or b; 6.14 (s,1H).

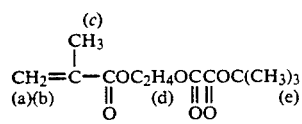

EXAMPLE 43

A 500 ml flask equipped with a decanter, a condenser, a stirrer and a dropping funnel was charged with 90 g of xylene and heated to 100° C. To the content, 39.0 g of t-butoxalyloxyethyl methacrylate of Example 42, 26.2 g of n-butyl acrylate, 34.8 g of methyl methacrylate and 2.0 g of azobisisobutylonitrile were added dropwise for 3 hours. After mixing for 30 minutes, 0.2 g of azobisisobutylonitrile and 10 g of xylene were added dropwise for one hour. After mixing with heating for 1.5 hours, the obtained solution was cooled to room temperature to obtain transparent and light yellow polymer. The polymer solution had a viscosity of 243 cps °C. (E type viscometer at 25° C.) and a nonvolatile content of 50% (130° C., one hour), and had Mn=6,790, Mw=13,300, α=1.96.

EXAMPLE 44

As generally described in Example 42, the reaction was conducted with the exception that 46.4 g (0.4 mol) of 2-hydroxyethyl acrylate was employed instead of 2-hydroxyethyl methacrylate to obtain 96.6 g (yield 98.8%) of t-butoxalyloxyethyl acrylate which was identified by IR and NMR.

IR (cm$^{-1}$, neat): 2950 (C—H), 1760-1720 (C=O), 1620 (C=C), 1140 (C—O).

$^1$H-NMR (ppm, in CDCl$_3$, TMS Standard): e; 1.54 (s,9H), d; 4.43-4.50 (m,4H), a or b; 5.88-5.90 (d,1H), c; 6.11-6.19 (d-d,1H), a or b; 6.42-6.47 (d,1H).

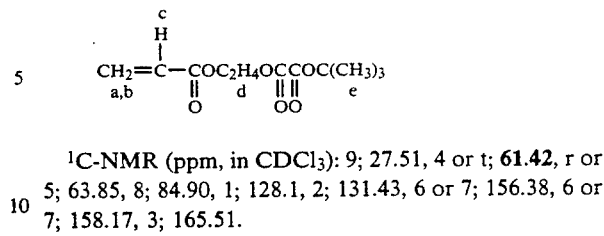

$^1$C-NMR (ppm, in CDCl$_3$): 9; 27.51, 4 or t; 61.42, r or 5; 63.85, 8; 84.90, 1; 128.1, 2; 131.43, 6 or 7; 156.38, 6 or 7; 158.17, 3; 165.51.

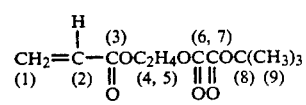

EXAMPLE 45

A 200 ml flask equipped with a decanter, a condenser, a stirrer and a dropping funnel was charged with 45 g of xylene and heated to 100° C. To the content, 36.6 g of t-butoxalyloxyethyl acrylate of Example 44, 7.7 g of n-butyl acrylate, 5.7 g of methyl methacrylate and 1.0 g of azobisisobutylonitrile were added dropwise for 3 hours. After mixing for 30 minutes, 0.1 g of azobisisobutylonitrile and 5 g of xylene were added dropwise for 30 minutes. After mixing with heating for 1.5 hours, the obtained solution was cooled to room temperature to obtain transparent and light yellow polymer. The polymer solution had a viscosity of 83 cps (E type viscometer at 25° C.) and a nonvolatile content of 49% (130° C., one hour), and had Mn=4,800, Mw=10,090, α=2.10.

EXAMPLE 46

A mixture was prepared by dissolving 92.6 g (0.5 mol) of SIPOMER TBM (t-butylaminoethyl methacrylate available from Arcolac Company) and 50.6 g (0.5 mol) of triethylamine in 400 ml of benzene and cooled to 2° C. A solution of 68.3 g (0.5 mol) of ethoxalyl chloride in 100 ml of benzene was added dropwise for one hour. After the completion of dropping it was allowed to mix for 1.5 hours without cooling to terminate reaction. The precipitated salt was filtered off and the filtrate was evaporated to obtain brown viscous liquid which was identified by IR and $^1$H-NMR to find N-t-butyl-N-ethoxalylaminoethyl methacrylate.

IR (cm$^{-1}$, neat): 1740, 1720, 1660 (C=O), $^1$H-NMR (ppm, in CDCl$_3$, TMS Standard) h; 1.36 (t,3H), f; 1.51 (s,9H), e; 3.58 (t,3H), c; 1.95 (s,3H), d and g; 4.30 (m,4H), a or b; 5.62 (S,1H), a or b; 6.15 (s,1H).

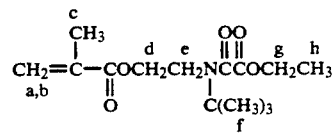

$^{13}$C-NMR (ppm, in CDCl$_3$) 12; 13.81, 3; 16.17, 8; 28.11, 6; 44.06, 7; 57.78 11; 61.85, 5; 63.25, 1; 126.29, 2; 135.64, 8 or 9; 163.15, 8 or 9; 163.53, 4; 166.66.

$$\underset{(1)}{CH_2}=\underset{(2)}{\overset{\overset{(3)}{CH_3}}{\underset{(4)}{C}}}-\underset{\underset{O}{\overset{\|}{}}}{\overset{}{C}}OCH_2CH_2\overset{(9)}{\underset{\underset{C(CH_3)_3}{|}}{N}}\overset{\overset{O\;O}{\overset{\|\;\|}{}}}{\underset{(7)\;(8)}{C}}COCH_2CH_3$$

EXAMPLE 47

A 200 ml flask equipped with a decanter, a condenser, a stirrer and a dropping funnel was charged with 35 f of xylene and heated to 135° C. To the content, 60.0 g of N-t-butyl-N-ethoxalylaminoethyl methacrylate of Example 46, 20.0 g of isobutylmethyl methacrylate, 10.0 g of styrene, 10.0 g of alpha-methylstyrene dimer and 10.0 g of Kaya Ester-O were added dropwise for 3 hours. After mixing for 30 minutes, 1.0 g of Kaya Ester-O and 8 g of xylene were added dropwise for one hour. After mixing with heating for 1.5 hours, the obtained solution was cooled to room temperature to obtain transparent and light yellow polymer. The polymer solution had a viscosity of 193 cps (E type viscometer at 25° C.) and a nonvolatile content of 64% (130° C., one hour), and had $Mn=1,345$, $Mw=1,990$, $\alpha=1.48$.

EXAMPLE 48

A three liter flask was charged with 253.86 g (2.0 mol) of oxalyl chloride and 1200 ml of benzene and cooled with stirring. A solution of 120.2 g (2.0 mol) of isopropyl alcohol, 212.5 g (2.0 mol) of triethylamine and 400 ml of benzene was added dropwise for 3 hours. After the completion of dropping, mixing was continued at 20° C. for 2 hours. The solution became blown and precipitated crystal. After adding 600 ml of hexane to the reaction mixture, the precipitated solid was filtered off and the filtrate was condensed. It was then distilled under vacuum to obtain 74.4 g (yield 17.7%) of isopropoxalyl chloride. (bp 100°–105° C./150 mmHg).

$^1$H-NMR (ppm: 1.38 (d,6H), 5.20 (m,1H).

Next, a 500 ml reaction vessel was charged with 25 g (0.17 mol) of the obtained isopropoxalyl chloride and 150 ml of benzene and cooled to 5° C. with ice. A mixture of 27.9 g (0.214 mol) of 2-hydroxyethyl methacrylate and 24.1 g (0.238 mol) of triethylamine was added dropwise for 1.5 hours with mixint while precipitating white solid. Mixing was continued at 5° C. for 1.5 hours and filtered. The filtrate was condensed and then distilled under vacuum to obtain 17.6 g (yield 43.3%) of isopropoxalyloxyethyl methacrylate of bp. 112° C./0.3 mm Hg.

IR (cm$^{-1}$, neat): 3500, 2980, 1760, 1740, 1720, 1635, 1095, 680.

$^1$H-NMR (ppm, in CDCl$_3$, TMS Standard) 1.33 (d,6H), 1.92 (s,3H), 4.41 (m,2H), 4.52 (m,2H), 5.17 (m,1H), 5.60 (s,1H), 6.12 (s,1H).

EXAMPLE 49

A 200 ml flask equipped with a decanter, a condenser, a stirrer and a dropping funnel was charged with 50 ml of xylene and heated to 110° C. To the content, 52.2 f of isopropoxalyloxyethyl methacrylate, 27.8 g of cyclohexyl methacrylate, 10.0 g of styrene, 10.0 g of alpha-methylstyrene dimer and 10.0 g of t-butylperoxy-2-ethyl hexanate were added dropwise for 3 hours. After mixing at 110° C. for 30 minutes, 1.0 g of t-butylperoxy-2-ethyl hexanate and 6.0 g of xylene were added dropwise for 30 minutes. It was then mixed at 110° C. for 1.5 hours to obtain a copolymer having a nonvolatile content of 58.6% (130° C., 60 minutes), and had $Mn=1,870$, $Mw=3,240$, $\alpha=1.73$.

EXAMPLE 50

An amount of 1 wt %/resin solid content of dibutyltin dilaurate was mixed with 2.36 g of the acryl polyol of Production Example 1 and 2.00 g of the polymer prepared in Example 47 to form a curable composition. The resultant composition was coated on a tin plate by a bar coater No. 40 in a thickness of 20 micrometers, and then baked at 180° C. for 30 minutes. The cured film had a gellation % (measured as Examle 35) of 95.3%.

What is claimed is:

1. A polymerizable compound represented by the formula (I)

$$A-X-COCOOR_1$$

wherein A represents a $C_3$–$C_{18}$, alkynyl, alkenylaryl or alkenylaralkyl group, or a group represented by $$CH=\underset{R_2}{\overset{\overset{}{|}}{C}}-\underset{\overset{\|}{O}}{\overset{}{C}}\left(Y-CH_2-\underset{\overset{|}{R_3}}{CH}\right)_n\left(\overset{\overset{O}{\overset{\|}{}}}{O}C(CH_2)_m\right)_l-$$

(wherein $R_2$ and $R_3$, which is the same or different, represents a hydrogen atom, or a $C_1$–$C_5$ alkyl group, Y represents an oxygen atom or —NR$_4$—, in which R$_4$ represents a hydrogen atom or a $C_1$–$C_5$ alkyl group, n is an integer of 1 to 5, m is an integer of 1 to 10 and l is 0 or an integer of 1 to 20.);

$R_1$ represents a $C_1$–$C_5$ alkyl group or an aryl group; and

X represents an oxygen atom, a sulfur atom, —COO— or —NR$_5$—, in which R$_5$ is a hydrogen atom or a $C_1$–$C_5$ alkyl group, provided that if Y is present, X is not —NR$_5$—.

2. The polymerizable compound according to claim 1 wherein said group A is a $C_3$–$C_{18}$ alkynyl group.

3. The polymerizable compound according to claim 1 wherein said group A is a $C_3$–$C_{18}$ alkenylaryl group.

4. The polymerizable compound according to claim 1 wherein said group A is a $C_3$–$C_{18}$ alkenylaralkyl group.

5. A polymerizable compound represented by the formula $$A-X-COCOOR_1$$

wherein A is a group represented by $$CH_2=\underset{R_2}{\overset{\overset{}{\|}}{C}}-\underset{\overset{\|}{O}}{\overset{}{C}}\left(Y-CH_2-\underset{\overset{|}{R_3}}{CH}\right)_n\left(\overset{\overset{O}{\overset{\|}{}}}{O}C(CH_2)_m\right)_l$$

wherein $R_2$ and $R_3$, which may be the same or different, each represents a hydrogen atom, or a $C_1$–$C_5$ alkyl group, Y represents an oxygen atom or —NR$_4$—, in which R$_4$ represents a hydrogen atom or a $C_1$–$C_5$ alkyl group, n is an integer of 1 to 5, m is an integer of 1 to 10, l is 0 or an integer of 1 to 20, $R_1$ represents a $C_1-C_5$ alkyl group or an aryl group,
X represents an oxygen atom, a sulfur atom, —COO— or —NR$_5$—, in which $R_5$ is a hydrogen atom or a $C_1-C_5$ alkyl group, provided that if Y is present, X is not —NR$_5$—.

6. The polymerizable compound according to claim 5 wherein said l is 0.

7. The polymerizable compound according to claim 6 wherein said X is an oxygen atom and said $R_1$ is ethyl.

* * * * *